United States Patent
Pang et al.

(10) Patent No.: US 12,108,936 B2
(45) Date of Patent: Oct. 8, 2024

(54) ANTI-FOGGING ENDOSCOPIC CAMERA SYSTEMS AND METHODS

(71) Applicant: Stryker Corporation, Kalamazoo, MI (US)

(72) Inventors: Chien Mien Pang, San Jose, CA (US); Levey Tran, Denver, CO (US)

(73) Assignee: Stryker Corporation, Kalamazoo, MI (US)

( * ) Notice: Subject to any disclaimer, the term of this patent is extended or adjusted under 35 U.S.C. 154(b) by 195 days.

(21) Appl. No.: 17/149,636

(22) Filed: Jan. 14, 2021

(65) Prior Publication Data

US 2021/0212555 A1 Jul. 15, 2021

Related U.S. Application Data

(60) Provisional application No. 62/961,622, filed on Jan. 15, 2020.

(51) Int. Cl.
*A61B 1/00* (2006.01)
*A61B 1/05* (2006.01)

(52) U.S. Cl.
CPC ...... *A61B 1/00126* (2013.01); *A61B 1/00137* (2013.01); *A61B 1/00188* (2013.01); *A61B 1/05* (2013.01)

(58) Field of Classification Search
CPC ............ A61B 1/00126; A61B 1/00137; A61B 1/00188; A61B 1/05; A61B 1/00128; A61B 1/042; A61B 1/253; A61B 1/127
USPC ........................................................ 600/112
See application file for complete search history.

(56) References Cited

U.S. PATENT DOCUMENTS

| | | | | |
|---|---|---|---|---|
| 5,205,280 A | * | 4/1993 | Dennison, Jr. ..... | A61B 1/00128 403/DIG. 4 |
| 5,836,867 A | * | 11/1998 | Speier ................ | G02B 23/2484 403/DIG. 1 |
| 5,868,664 A | * | 2/1999 | Speier .................... | A61B 1/042 600/134 |
| 6,077,220 A | * | 6/2000 | Rudischhauser .. | G02B 23/2476 600/162 |
| 6,170,167 B1 | * | 1/2001 | Kato .................. | G02B 27/0006 34/95 |
| 7,896,800 B2 | | 3/2011 | Renner et al. | |
| 8,840,543 B2 | * | 9/2014 | Deng ................. | A61B 1/00112 600/109 |
| 9,615,725 B2 | | 4/2017 | Deng et al. | |

(Continued)

FOREIGN PATENT DOCUMENTS

DE 19647851 A1 2/1998

*Primary Examiner* — John P Leubecker
*Assistant Examiner* — Li-Ting Song
(74) *Attorney, Agent, or Firm* — Morrison & Foerster LLP (57) ABSTRACT

A coupler for coupling an endoscope to an endoscopic camera head is configured for removably mounting to a portion of the camera head that houses at least one imaging sensor and includes a housing assembly forming a sealed chamber that houses at least one optical component for focusing light for the at least one imaging sensor, and at least one desiccant component that is in air communication with the sealed chamber for absorbing moisture from the sealed chamber, wherein the at least one desiccant component comprises a desiccant that is at least partially covered by at least one covering to prevent desiccant particulates from entering the sealed chamber.

18 Claims, 10 Drawing Sheets

(56) References Cited

U.S. PATENT DOCUMENTS

| | | | | |
|---|---|---|---|---|
| 2004/0127768 A1* | 7/2004 | Huber | A61B 1/00195 600/162 |
| 2006/0069308 A1* | 3/2006 | Renner | A61B 1/00195 600/133 |
| 2012/0283515 A1* | 11/2012 | Buerk | A61B 1/00066 600/153 |
| 2013/0342906 A1* | 12/2013 | Dahmen | G02B 23/2476 359/513 |
| 2014/0275781 A1* | 9/2014 | Deng | A61B 1/0011 600/109 |
| 2017/0172701 A1* | 6/2017 | Kube | G06K 19/07758 |
| 2017/0347861 A1* | 12/2017 | Deutschendorf | A61B 1/0011 |
| 2020/0015661 A1* | 1/2020 | Berkner | A61B 1/00128 |

\* cited by examiner

ANTI-FOGGING ENDOSCOPIC CAMERA SYSTEMS AND METHODS

CROSS-REFERENCE TO RELATED APPLICATIONS

This application claims the benefit of U.S. Provisional Application No. 62/961,622, filed Jan. 15, 2020, the entire contents of which are hereby incorporated by reference herein.

FIELD OF THE DISCLOSURE

The present invention pertains to the field of medical devices. More particularly, the present invention relates to endoscopic camera systems.

BACKGROUND OF THE DISCLOSURE

An endoscopic camera system includes an endoscope that is inserted into the body of a subject for delivering light to and receiving light from a surgical cavity. The endoscope is mounted to a camera head that can capture video and images based on the light received from the endoscope. The camera head is communicatively coupled to a camera control unit that processes video and image data from the camera head for display or storage.

An optical coupler is generally used to connect the endoscope to the camera head and can include optical components for focusing the light received from the endoscope onto the imaging sensor assembly in the camera head. To provide this focusing function, a coupler may include one or more optical components, such as one or more lenses or prisms, that can be moved relative to the camera, the endoscope, or both, to alter the focal distance.

Because the coupler is used in the medical operating environment, sterilization is necessary between uses. Steam autoclaving is a common method of sterilization and is used for many medical instruments that can withstand the necessary high temperature and pressure. Instruments that will not survive the autoclave process can be sterilized by low temperature sterilization techniques, such as immersion in sterilization liquid or gas.

Optical systems can be very sensitive to condensation caused by moisture, particularly the moisture of a sterilizing environment. Moisture from sterilization that penetrates into the interior of the optical chamber can cause fogging (condensation) on lenses and other optical components, which can reduce the quality of images generated by the camera head. Couplers can be configured with seals or water proof adhesives to prevent moisture accumulation in the coupler.

SUMMARY OF THE DISCLOSURE

According to some embodiments, a coupler for a camera head includes a sealed chamber housing one or more optical components and one or more desiccant components located in air communication with the sealed chamber to absorb moisture that may penetrate through the seals over time due to repeated sterilizations. According to some embodiments, the desiccant components are located near the optical components providing better humidity control and a more compact design. To prevent desiccant particulates from falling onto the optical components due to the proximity of the desiccant components to the optical components, a breathable layer is provided over the desiccant material, which blocks particulates from migrating into the sealed chamber. By providing desiccant in the coupler for absorbing moisture that migrates through seals due to repeated sterilizations and providing a barrier that prevents desiccant particulates from falling onto optical components, the lifespan of the coupler can be increased without requiring costly and bulky seal configurations.

According to some embodiments, a coupler for coupling an endoscope to an endoscopic camera head is configured for removably mounting to a portion of the camera head that houses at least one imaging sensor and a housing assembly forming a sealed chamber that houses at least one optical component for focusing light for the at least one imaging sensor, and at least one desiccant component that is in air communication with the sealed chamber for absorbing moisture from the sealed chamber, wherein the at least one desiccant component comprises a desiccant that is at least partially covered by at least one covering to prevent desiccant particulates from entering the sealed chamber.

In any of these embodiments, the coupler can be configured to be sterilized when dismounted from the portion of the camera head.

In any of these embodiments, the coupler can include a first light transmissive component sealing a first end of the sealed chamber and a second light transmissive component sealing a second end of the sealed chamber. In any of these embodiments, at least one of the first and second light transmissive components can be adhesively attached to the housing assembly.

In any of these embodiments, the at least one optical component can include an optical assembly that comprises an optical assembly housing that houses the at least one optical component. In any of these embodiments, the optical assembly can include a plurality of optical components that are fixedly mounted to the optical assembly housing.

In any of these embodiments, the at least one optical component can be movable within the chamber for focus adjustment.

In any of these embodiments, the at least one desiccant component can be located in at least one pocket and at least one air pathway can lead from the at least one pocket to the sealed chamber.

In any of these embodiments, the at least one desiccant component can be located in the sealed chamber. In any of these embodiments, the at least one desiccant component can be shaped as a ring.

In any of these embodiments, the desiccant that is at least partially covered by the at least one covering can be formed as a single solid.

In any of these embodiments, the at least one desiccant component can include a plurality of spaced apart desiccant components.

In any of these embodiments, the at least one desiccant component can be shaped as a tablet.

In any of these embodiments, the at least one desiccant component can be shaped as a ring.

In any of these embodiments, the at least one desiccant component can include at least one of silica gel, activated charcoal, calcium chloride, charcoal sulfate, activated alumina, Montmorillonite clay, and molecular sieve.

In any of these embodiments, the sealed chamber can be at least partially sealed by at least one elastomeric seal.

In any of these embodiments, the coupler can include a focusing member for engagement by a user for adjusting a location of the at least one optical component within the sealed chamber and at least one elastomeric seal that seals between the focusing member and the housing assembly.

In any of these embodiments, the housing assembly can include a plurality of components that are assembled together and at least partially sealed by one or more elastomeric seals.

According to some embodiments, an endoscopic camera head includes a main housing that houses at least one imaging sensor; and a coupler removably mounted to the main housing and configured for coupling an endoscope to the camera head, the coupler including a housing assembly forming a sealed chamber that houses at least one optical component for focusing light for the at least one imaging sensor, and at least one desiccant component that is in air communication with the sealed chamber for absorbing moisture from the sealed chamber, wherein the at least one desiccant component comprises a desiccant that is at least partially covered by at least one covering to prevent desiccant particulates from entering the sealed chamber.

In any of these embodiments, the coupler can be configured to be removed from the main housing and sterilized.

In any of these embodiments, the coupler can include a first light transmissive component sealing a first end of the sealed chamber and a second light transmissive component sealing a second end of the sealed chamber. In any of these embodiments, at least one of the first and second light transmissive components can be adhesively attached to the housing assembly.

In any of these embodiments, the at least one optical component can include an optical assembly that comprises an optical assembly housing that houses the at least one optical component. In any of these embodiments, the optical assembly can include a plurality of optical components that are fixedly mounted to the optical assembly housing.

In any of these embodiments, the at least one optical component can be movable within the chamber for focus adjustment.

In any of these embodiments, the at least one desiccant component can be located in at least one pocket and at least one air pathway leads from the at least one pocket to the sealed chamber.

In any of these embodiments, the at least one desiccant component can be located in the sealed chamber. In any of these embodiments, the at least one desiccant component can be shaped as a ring.

In any of these embodiments, the desiccant that is at least partially covered by the at least one covering can be formed as a single solid.

In any of these embodiments, the at least one desiccant component can include a plurality of spaced apart desiccant components.

In any of these embodiments, the at least one desiccant component can be shaped as a tablet.

In any of these embodiments, the at least one desiccant component can be shaped as a ring.

In any of these embodiments, the at least one desiccant component can include at least one of silica gel, activated charcoal, calcium chloride, charcoal sulfate, activated alumina, Montmorillonite clay, and molecular sieve.

In any of these embodiments, the sealed chamber can be at least partially sealed by at least one elastomeric seal.

In any of these embodiments, the coupler can include a focusing member for engagement by a user for adjusting a location of the at least one optical component within the sealed chamber and at least one elastomeric seal that seals between the focusing member and the housing assembly.

In any of these embodiments, the housing assembly can include a plurality of components that are assembled together and at least partially sealed by one or more elastomeric seals.

According to some embodiments, an endoscopic camera head includes a main housing that houses at least one imaging sensor and includes a sealed chamber that houses at least one optical component for focusing light for the at least one imaging sensor, and at least one desiccant component that is in air communication with the sealed chamber for absorbing moisture from the sealed chamber, wherein the at least one desiccant component comprises a desiccant that is at least partially covered by at least one covering to prevent desiccant particulates from entering the sealed chamber.

According to some embodiments, an endoscope includes a main housing that houses at least one optical component for receiving endoscopic imaging light and includes a sealed chamber that houses the at least one optical component, and at least one desiccant component that is in air communication with the sealed chamber for absorbing moisture from the sealed chamber, wherein the at least one desiccant component comprises a desiccant that is at least partially covered by at least one covering to prevent desiccant particulates from entering the sealed chamber.

According to some embodiments, a method includes sterilizing a coupler configured to couple an endoscope to an endoscopic camera head main body, the coupler comprising a housing assembly forming a sealed chamber that houses at least one optical component for focusing light for the at least one imaging sensor, and at least one desiccant component that is in air communication with the sealed chamber for absorbing moisture from the sealed chamber, wherein the at least one desiccant component comprises a desiccant that is at least partially covered by at least one covering to prevent desiccant particulates from entering the sealed chamber; and capturing one or more images via the endoscopic camera head with attached coupler.

In any of these embodiments, the coupler can be separated from the camera head main body for sterilization.

In any of these embodiments, the coupler can be attached to the camera head main body for sterilization.

BRIEF DESCRIPTION OF THE DRAWINGS

The invention will now be described, by way of example only, with reference to the accompanying drawings, in which.

DETAILED DESCRIPTION OF THE DISCLOSURE

Reference will now be made in detail to implementations and embodiments of various aspects and variations of systems and methods described herein. Although several exemplary variations of the systems and methods are described herein, other variations of the systems and methods may include aspects of the systems and methods described herein combined in any suitable manner having combinations of all or some of the aspects described.

According to various embodiments, an endoscopic camera head for use in endoscopic procedures includes a coupler that couples an endoscope to the camera head. The coupler is an opto-mechanical device that receives light from a scene via the attached endoscope and focuses the light onto an image sensor assembly within the camera head. Generally, after each surgery, the coupler is washed and sterilized to ensure that the coupler is clean and sterile before the next use.

If any moisture were to migrate into the optical chamber of the coupler during the washing and sterilization processes, fogging of one or more optical components could occur, which could degrade image quality. To prevent accumulation of moisture in the optical chamber, the coupler includes a plurality of sealing interfaces, such as o-ring seals and adhesively attached components. However, the inventors surprisingly discovered that moisture is able to migrate through the sealing interfaces over time due to repeated washing and sterilization procedures that occur over the lifespan of the coupler. For example, elastomeric materials used in o-rings have a degree of moisture permeability that can allow moisture to migrate through the seals over time, and adhesives can break down over time due to exposure to moisture and heat during washing and sterilization.

Moisture that migrates through seals and adhesive interfaces can accumulate to the degree that fogging of one or more optical components within the coupler occurs. The inventors also surprisingly discovered that the risk of fogging is exacerbated by the decreasing size of couplers designed to meet the requirements for smaller and lighter weight camera heads. Increased compactness leads to decreased air volume within the sealed portion of the coupler. This decreased air volume can reach a relative humidity that can lead to fogging sooner than a less compact design that has a greater air volume.

To extend the lifespan of the coupler, particularly in a compact coupler configuration, embodiments described herein include desiccant located so as to be in air communication with the sealed optical chamber. Thus, moisture that migrates through the seals and adhesive interfaces is absorbed by the desiccant, preventing fogging of optical components and degradation of image quality.

According to various embodiments, the desiccant is located close to the optical components to ensure that the humidity in the optical chamber is well controlled and due to the compact design of the coupler, which can increase the risk that desiccant particulates fall onto one or more optical components. To mitigate this risk, the desiccant is formed into a solid and at least partially covered by a breathable layer that allows moisture to pass into the desiccant while preventing desiccant particulates from breaking away and falling onto one or more optical components.

According to various embodiments, couplers having desiccant according to the principles described herein can be sterilized using autoclaving. According to various embodiments, couplers having desiccant according to the principles described herein can be sterilized using low temperature sterilization.

In the following description of the various embodiments, reference is made to the accompanying drawings, in which are shown, by way of illustration, specific embodiments that can be practiced. It is to be understood that other embodiments and examples can be practiced, and changes can be made without departing from the scope of the disclosure.

In addition, it is also to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain terminology is used in this description for convenience and reference only, and is not limiting. For example, the words "upwardly," "downwardly," "rightwardly," and "leftwardly" refer to directions in the drawings to which reference is made. The words "inwardly" and "outwardly" refer to directions toward and away from, respectively, the geometric center of the arrangement and designated parts thereof. The words "forwardly" and "distally" refer to the direction toward the end of the arrangement that is closest to the subject, and the words "rearwardly" and "proximally" refer to the direction toward the end of the arrangement which is furthest from the subject. This terminology includes the words specifically mentioned, derivatives thereof, and words of a similar nature.

Figure 1:
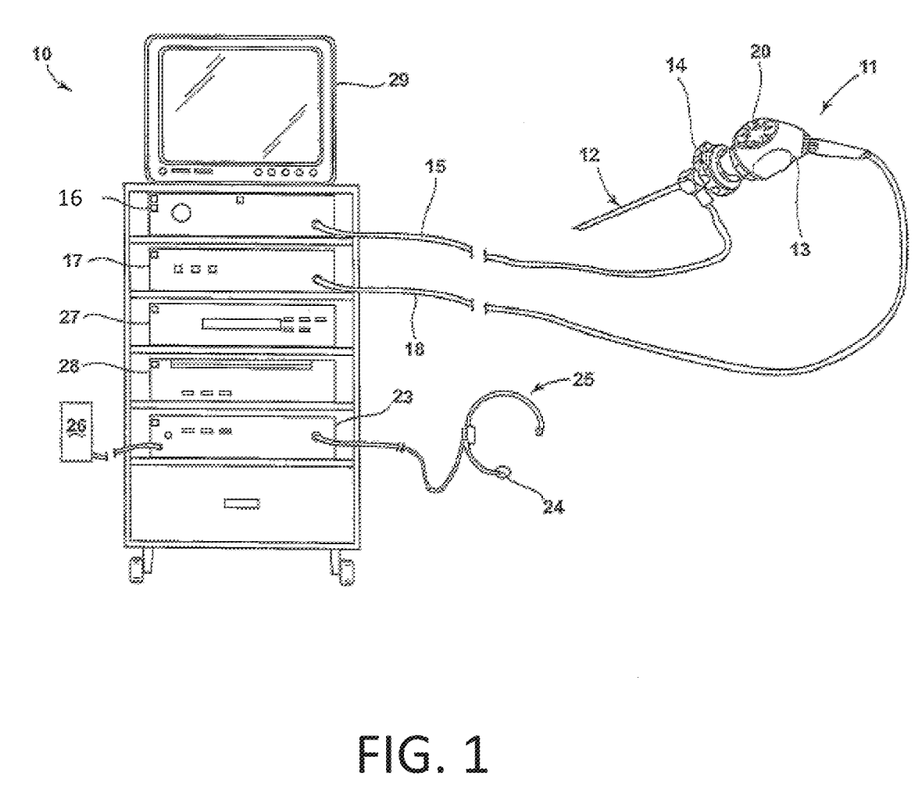
FIG. 1 illustrates an endoscopic imaging system, according to various embodiments.

FIG. 1 illustrates an endoscopic imaging system 10, according to various embodiments. Endoscopic imaging system 10 includes an endoscope assembly 11 that can be used for visualizing inside of a subject's body during an endoscopic procedure. The endoscope assembly 11 includes an endoscope 12 coupled to a camera head 13 by a coupler 14 that forms the distal portion of the camera head 13. Light is provided to the endoscope 12 by a light source 16 via a light cable 15, which can be, for example, a fiber optic cable. The endoscope 12 directs the light from the light cable 15 to the area of interest within the subject's body, receives light reflected from the area of interest, and conveys light to the imager within the camera head 13. The imager is comprised of one or more image sensors which converts the optical image into electrical signals.

The camera head 13 may be coupled to a camera control unit (CCU) 17 by a camera cable 18. The camera cable 18 can convey imaging data from the camera head 13 to the CCU 17 for display on display 29. In some embodiments, various control signals are transmitted bi-directionally between the camera head 13 and the CCU 17 via the camera cable 18.

A user interface 20 can be provided on the camera head 13 for enabling a user to manually control various functions of the endoscopic imaging system 10. According to some embodiments, various functions of the endoscopic imaging system 10 may be controlled by voice commands received by a microphone 24 mounted on a headset 25 worn by the surgeon and coupled to the voice-control unit 23, which can be coupled to the CCU 17. A hand-held control device 26, such as a tablet with a touch screen user interface, may be coupled to the voice-control unit 23 as a further control interface. In some embodiments, an imaging system controller 27 can be included and connected to one or more system components, such as the CCU 17 and/or the light source 16. According to various embodiments, the imaging system controller 27 provides further processing of image data from the CCU 17, controls display and storage of image data and communication of imaging or other data to a hospital network, and/or communicates control commands to connected system components. In some embodiments, a printer 28 may be included for printing hard copies of one or more images.

Figure 2:
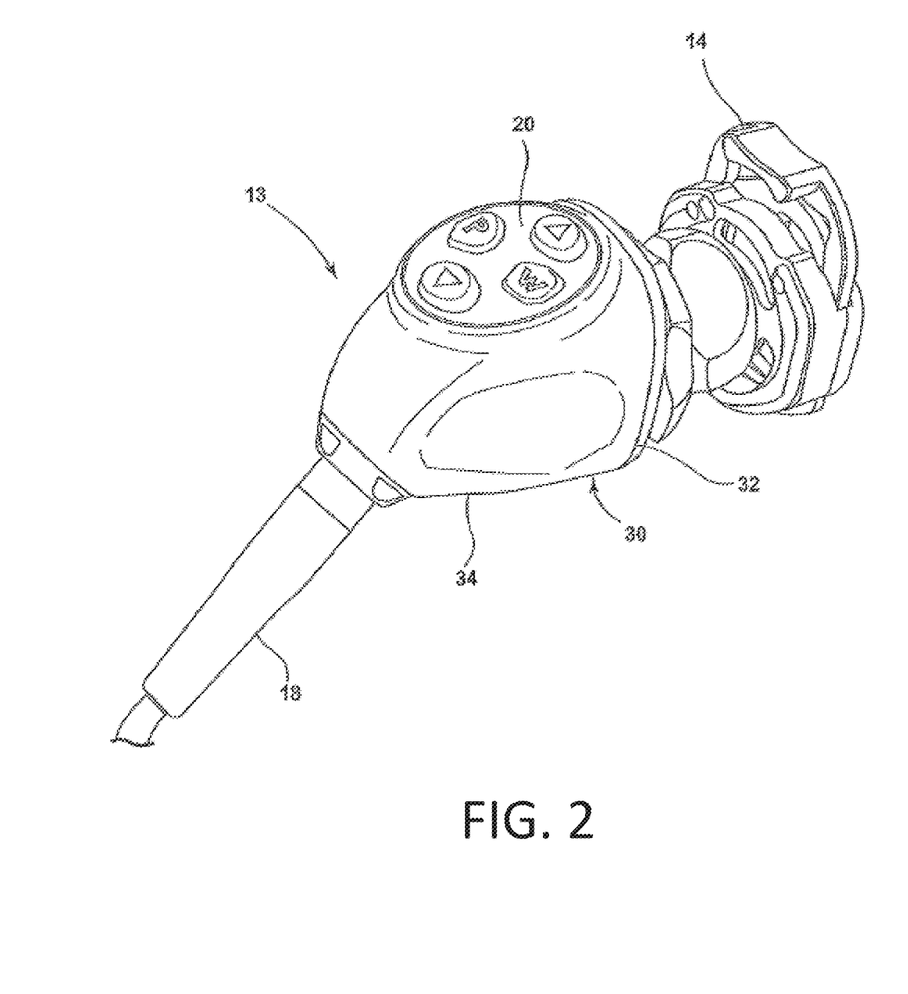
FIG. 2 is a perspective view of a camera head of the endoscopic imaging system, according to various embodiments.

FIG. 2 is a perspective view of camera head 13 of the endoscopic imaging system 10, according to various embodiments. The camera head 13 includes a main enclosure 30 and a coupler 14 that extends forwardly from the main enclosure 30. The main enclosure 30 can include two main enclosure parts-a front enclosure part 32 and a rear enclosure part 34. The user interface 20 can be sealably attached to the rear enclosure part 34, as described, for example, in commonly-owned U.S. Pat. No. 8,115,126, which is hereby incorporated by reference in its entirety. The coupler 14 extends forward of the front enclosure part 32 and can be removably mounted to the front enclosure part 32, such as via a threaded engagement. The camera cable 18 may extend from the rear enclosure part 34.

Figure 3:
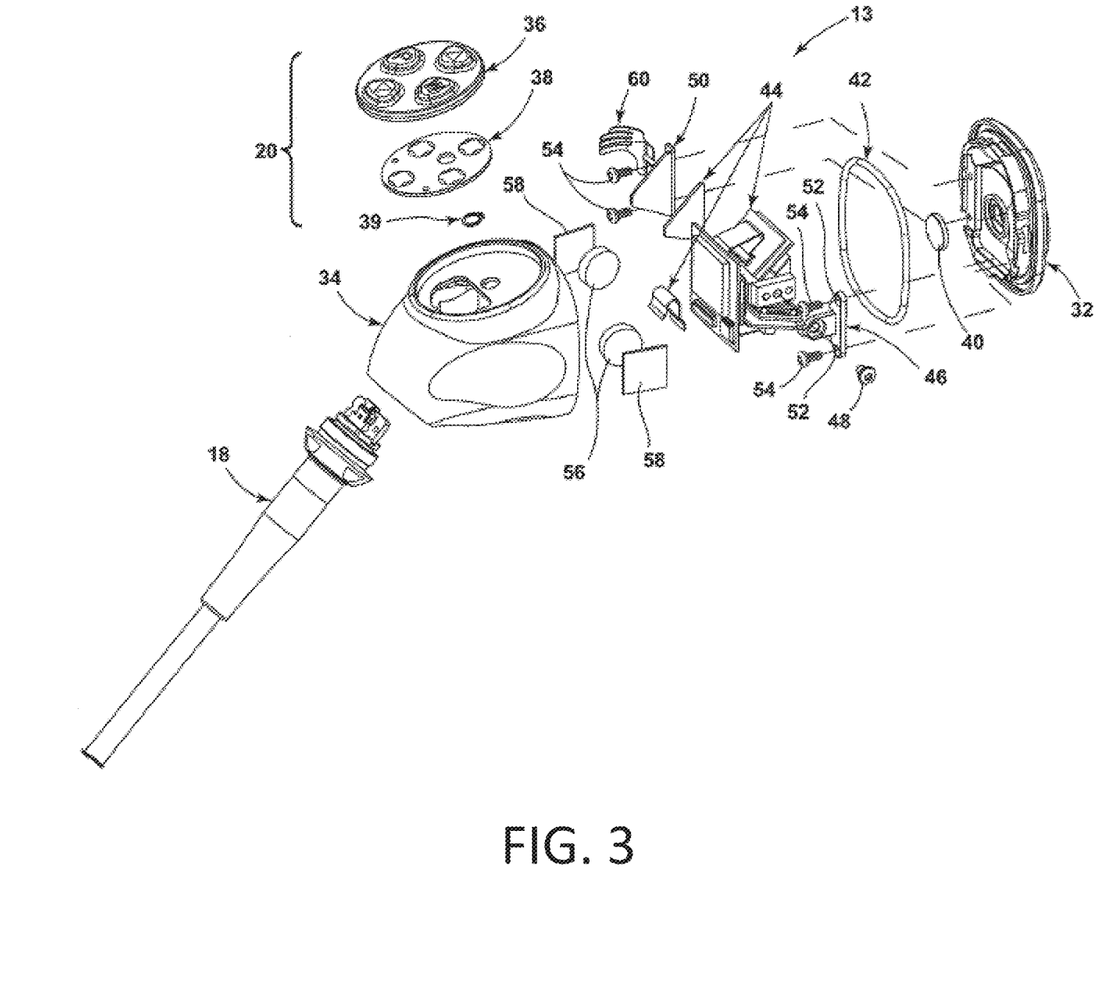
FIG. 3 is an exploded view of portions of a camera head that are housed within the main enclosure, according to some embodiments.

FIG. 3 is an exploded view of portions of the camera head 13 that are housed within the main enclosure 30, according to some embodiments. A window 40 can be sealably attached to the front enclosure part 32, such as via an adhesive, to seal the main enclosure 30. An O-ring 42 can be used to provide a seal between the front and rear enclosure parts 32, 34. An imaging sensor assembly 44 includes one or more imaging sensors for sensing light received from the scene via the endoscope 12. The imaging sensor assembly 44 can be attached to brackets 46 and 50, such as via fasteners 48, that can mount the imaging sensor assembly 44 to the front enclosure part 32 via fasteners 54.

In some embodiments, a connection spring 60 can be attached to the imaging sensor assembly 44 via the bracket 50 to allow engagement of the imaging sensor assembly 44 with the rear enclosure part 34 for further imaging sensor assembly support. The imaging sensor assembly 44, through the rear enclosure part 34, is attached to the camera cable 18 for connection with the CCU 17, as described above.

One or more desiccant components 56 can be provided in the camera head 13. The desiccant components can include a solid desiccant material, such as in a tablet shape, that are at least partially covered by a breathable layer that allows moisture in the air within the camera head to be absorbed by the desiccant, as discussed in more detail below. The one or more desiccant components 56 can be attached to the rear enclosure part 34 via any suitable attachment means, such as via an adhesive tape 58.

Figure 4:
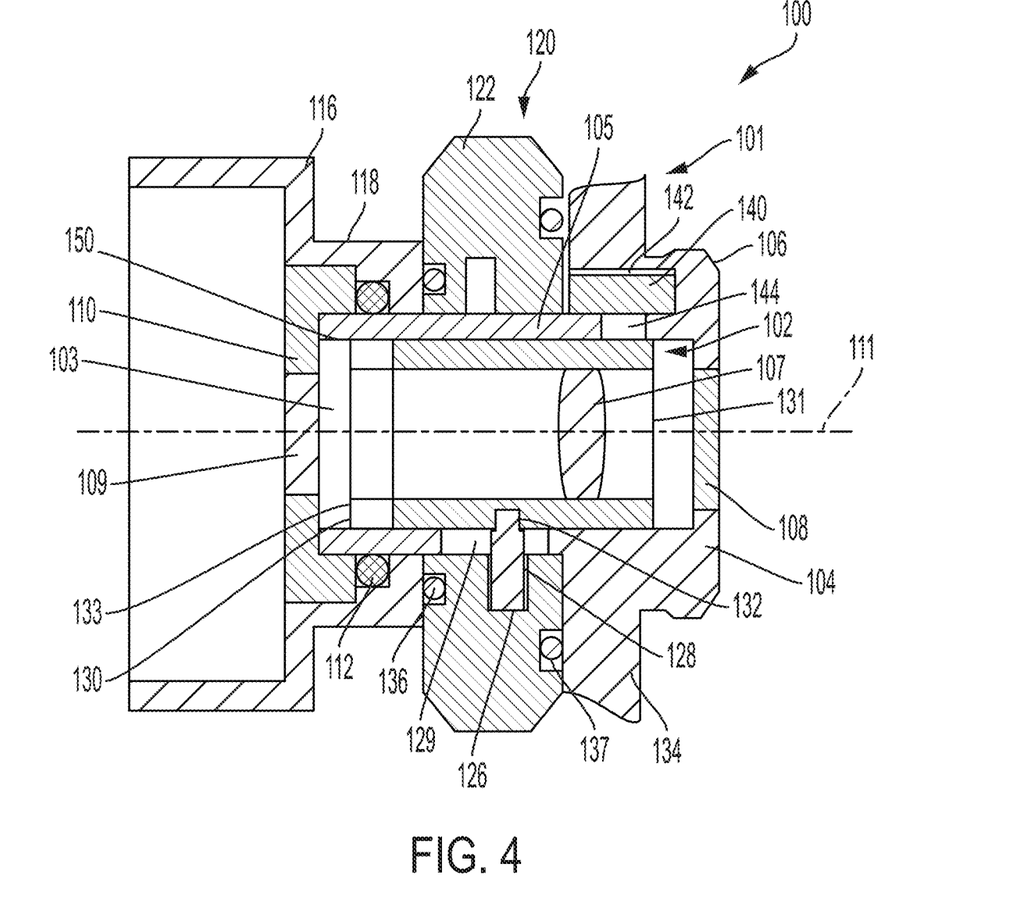
FIG. 4 is a cross section of a coupler that can be incorporated into a camera head, according to some embodiments.

FIG. 4 is a cross section of a coupler 100 that can be incorporated into a camera head, such as camera head 13, according to some embodiments. The coupler 100 can be removably attached to the main enclosure 30, which can allow the coupler 100 to be swapped out and/or washed and sterilized separately from the rest of the camera head. Coupler 100 can be sterilized via any suitable sterilization method, including low-temperature sterilization.

Coupler 100 includes a coupler housing assembly 101 that houses an optical assembly 102 for conveying light (e.g., focusing) received from an endoscope prior to the imaging sensor assembly 44 within the main enclosure 30. The coupler housing assembly 101 includes a rear adapter 104 that includes a coupling portion 106 for coupling with the main enclosure 30, such as via a threaded engagement with the front enclosure part 32. The coupling portion 106 can be, for example, a C-mount thread.

The optical assembly 102 is located within a chamber 103 formed by an inner wall 105 of the rear adapter 104. The optical assembly 102 can include one or more optical components 107, such as one or more lenses and/or prisms, for focusing light received from an endoscope onto the imaging sensor assembly housed in the main enclosure 30. The optical components 107 may be mounted within an optical assembly housing 130. The optical assembly housing 130 can have a rear opening 131 and may include a front piece 133 that fits to the optical assembly housing 130 for retaining the optical components 107 therein. As discussed further below, the optical assembly 102 can be slidably received in the chamber 103 and its forward-rearward position can be adjusted for focusing. In these embodiments, the inner surface 150 of the inner wall 105 of the rear adapter 104 can provide a bearing surface for the radially outer surface of the optical assembly housing 130 to enable the optical assembly 102 to slide within the chamber 103.

To prevent ingress of moisture into the chamber 103 within which the optical assembly 102 is located, the chamber 103 is sealed by front and rear windows 108 and 109. The rear window 108 can be affixed to the rear adapter 104 in such a way that a seal is formed between the rear adapter 104 and the rear window 108, such as via an adhesive that forms an adequate seal.

The front window 109 is affixed to a front retainer 110 that mounts to a front end of the rear adapter 104. The front window 109 can be affixed to the front retainer 110 in similar fashion to the fixing of the rear window 108 to the rear adapter 104. The front retainer 110 can mount to the front end of the rear adapter 104 via a threaded engagement or other suitable engagement.

An endobody clamp 116 is provided at the front end of the coupler 100 for releasably clamping an endoscope to the front end of the coupler 100. The endobody clamp 116 may be configured to repeatably position an endoscope relative to the coupler 100 such that the endoscope's optical axis (not shown) is aligned with the optical axis 111 of the optical assembly 102. The endobody clamp 116 includes a mounting collar 118 that mounts to the rear adapter 104 behind the front retainer 110 such that the front retainer 110 retains the endobody clamp 116 on the rear adapter 104.

Mounted rearward of the mounting collar 118 of the endobody clamp 116 is a focusing assembly 120 that is translationally retained between the mounting collar 118 and a flange 134 of the rear adapter 104. The focusing assembly 120 can be used to move the optical assembly 102, or one or more lenses of an optical assembly, within the chamber 103 along the optical axis 111 for focusing. The focusing assembly 120 can include a focus ring 122 that a user may grasp and rotate relative to the rear adapter 104. The focus ring or component interfaced with the focus ring may couple with a pin 128 that is mounted in a receiving bore 132 in the optical assembly housing 130 and extends through a longitudinally extending slot 129 in the inner wall 105 of the rear adapter 104 into the helical groove 126 of the focus ring 122 or component coupled to the focus ring 122. Via user rotation of the focus ring 122 (or, in some embodiments, via powered rotation of a focus ring or similar component), the pin 128 slides within the helical groove 126, which moves the pin 128 forward or backward within the slot 129, depending on the direction of rotation. This movement of the pin 128 causes the optical assembly 102 to slide along the optical axis 111 within the chamber 103, changing the focus provided by the coupler 100.

One or more seals can be used to ensure that the chamber 103 is sealed from ingress of moisture into the chamber 103. As illustrated in FIG. 4, a seal 112 (e.g., an o-ring) can be provided between the front retainer 110 and the mounting collar 118 of the endobody clamp 116. A second seal 136 can be provided on the front end of the focus ring 122, between the focus ring 122 and the mounting collar 118, and a third seal 137 can be provided on the rear end of the focus ring 122, between the focus ring 122 and the flange 134 of the rear adapter 104. This arrangement of seals is merely exemplary. Any suitable number, configuration, and location of seals can be used to prevent or retard ingress of moisture into the chamber 103.

The seals 112, 136, and 137 in combination with the sealed windows 108 and 109 seal the chamber 103 from ingress of moisture. However, as discussed above, over time and through repeated washings and sterilizations, it can be possible for moisture to migrate through the seals and/or adhesives and humidify the chamber 103. The relatively small volume of air within the sealed chamber 103 can exacerbate humidification since less moisture would need to migrate into the chamber 103 relative to a larger sealed chamber to reach the same relative humidity. As noted above, humidification of the sealed chamber 103 can lead to fogging on one or more surfaces of the optical components 107 of the optical assembly 102 and/or onto the windows 108, 109, which could degrade image quality. To prevent this fogging, the coupler 100 includes one or more desiccant components 140 for absorbing moisture that may be within the chamber 103.

In the illustrated embodiment, a desiccant component 140 is located in a pocket 142 in the flange 134 of the rear adapter 104. An opening 144 is formed in the inner wall 105 of the rear adapter 104 and provides an air communication path from the chamber 103 to the pocket 142 so that humidity in the chamber 103 can be drawn into the desiccant component 140. The desiccant component 140 is located quite near the chamber 103 in the illustrated embodiments, separated only by the thickness of the inner wall 105 of the rear adapter 104. As discussed further below, the desiccant component includes a layer of breathable material that is positioned so that it separates the desiccant material within the desiccant component from the opening 144 so that any desiccant particulates are prevented from passing through the opening 144 into the chamber 103.

Figure 5:
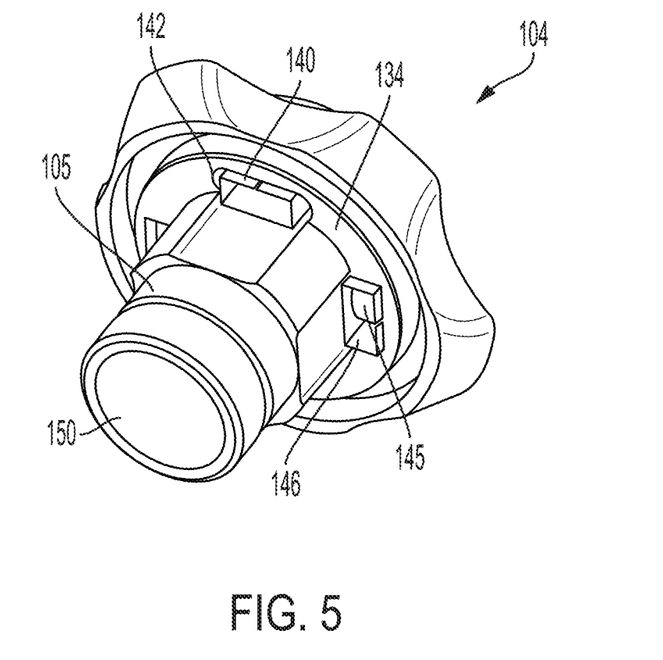
FIG. 5 is a perspective view of a rear adapter of a coupler, according to some embodiments.

FIG. 5 is a perspective view of the rear adapter 104, according to some embodiments, which illustrates an exemplary configuration of pockets 142 for desiccant components 140. In the illustrated embodiment, four desiccant components 140 are provided in each of four separate pockets 142 in the flange 134 (the fourth is out of view) such that the desiccant components 140 are even spaced circumferentially around the chamber 103. Any suitable number of desiccant components can be provided in any number of pockets, according to various embodiments. The size, number, and shape of desiccant components can be selected based on the space available for forming pockets 142 (or other desiccant component locations) in combination with the amount of desiccant required to maintain a sufficiently low level of humidity over the target lifespan of the coupler 100, given the volume of the chamber, the rate of moisture migration through the various seals, as well as predictions for the rates of washings/sterilizations.

Figure 6A:
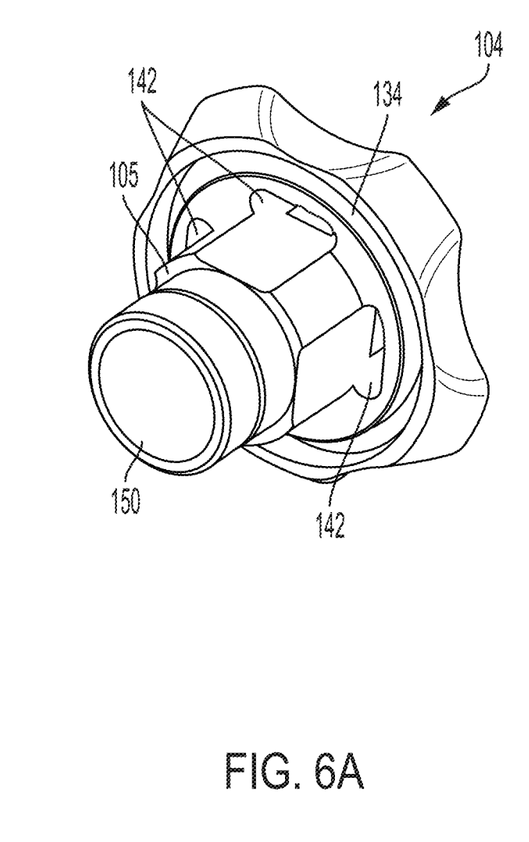
FIGS. 6A and 6B illustrate one manner of forming pockets and apertures in a coupler, according to some embodiments.
Figure 6B:
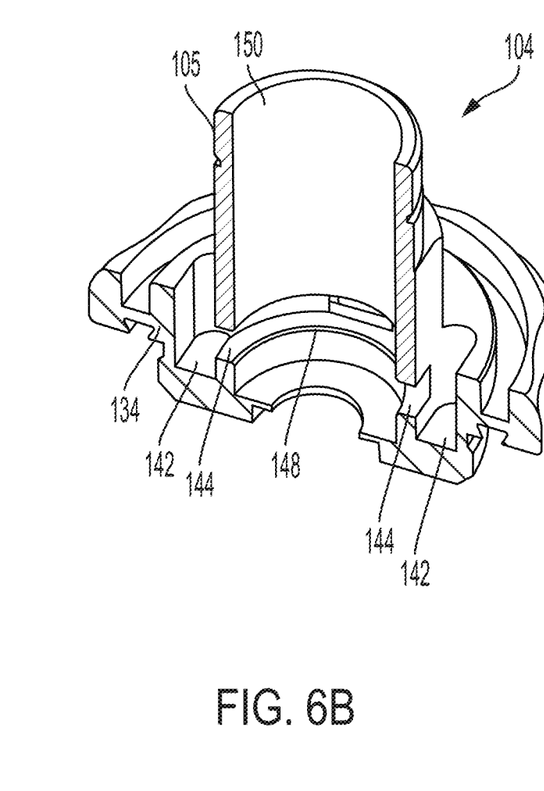

FIGS. 6A and 6B illustrate one manner of forming the pockets 142 and openings 144 in a way that maximizes the available space for desiccant without sacrificing coupler compactness, according to some embodiments. The pockets 142 are machined or otherwise formed into the flange 134 of the rear adapter 104. An annular groove 148 is machined or otherwise formed in the inner wall 105 of the rear adapter 104, extending from the inner surface 150 radially outwardly to a diameter that is sufficient such that the groove 148 connects with the pockets 142, thus forming the openings 144 that provide air communication between the pockets 142 and the chamber 103. Positioning of the pockets 142 in the flange 134 allows for the positions of desiccant components 140 in air communication with the chamber while not requiring significant increases in size of the coupler 100, which could otherwise be required if the desiccant were positioned, for example, directly in the chamber 103.

Figure 7:
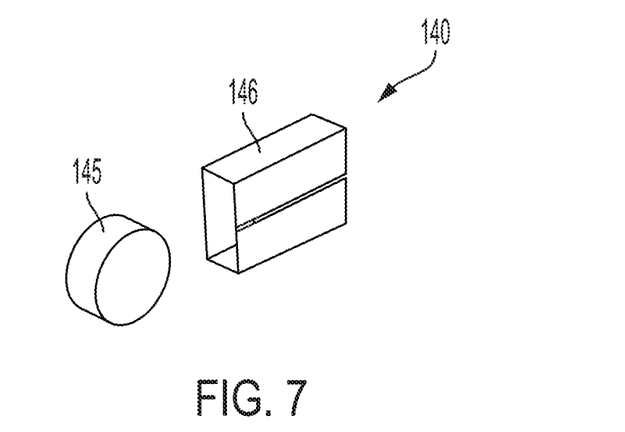
FIG. 7 is an exploded view of a desiccant component, according to some embodiments.

As shown in FIGS. 4-6, the one or more desiccant components 140 are located in close proximity to the chamber 103 housing optical components. Placement of the desiccant components 140 near the chamber 103 housing the optical components can ensure that humidity within the chamber 103 is well controlled. This advantage may not be achieved by placing the desiccant further from the optical components, such as, for example, placing the desiccant in a different part of a camera head assembly in embodiments in which the coupler and camera head main enclosure form a single sealed enclosure. However, this close proximity of the desiccant to the optical components increases the risk that desiccant particulates could migrate to the optical components or windows. While desiccant material can be formed into solids, desiccant is generally chalky and can relatively easily create particulates. To prevent desiccant particulates from entering the sealed chamber 103, the desiccant components 140 are formed of a solid desiccant material that is at least partially covered by a layer that prevents desiccant particulates from dislodging from the desiccant components 140 and falling into the chamber 103, as mentioned above. FIG. 7 is an exploded view of desiccant component 140 illustrating the partial covering of a solid molded desiccant 145 by a breathable layer 146, according to some embodiments. The breathable layer 146 serves to block desiccant particulates from entering the chamber 103 via the opening 144 while allowing humidity to pass to the desiccant 145.

The breathable layer 146 can be formed from a layer of breathable flexible material with an adhesive on one or both sides to keep the material in place on the desiccant and/or in the pocket. The material used for the breathable layer should be sufficiently porous to allow the desiccant to absorb moisture at a sufficiently high rate while not allowing desiccant particulates to migrate through. Examples of suitable breathable layer materials include medical grade materials, such as 3M™ Micropore™ Surgical Tape, 3M™ Medical Release Liner 1361, and 3M™ Medical Tape 9834, which were, to varying degrees, unexpectedly found to have the ideal combination of desiccant particulate retention and breathability in various embodiments.

Breathability of material can be judged by the material's moisture vapor transition rate (often referred to as MVTR). According to some embodiments, the breathable layer 146 is made from a medical grade tape having an MVTR of at least 100 g/m²/24 hr, at least 400 g/m²/24 hr, at least 600 g/m²/24 hr, at least 800 g/m²/24 hr, at least 1000 g/m²/24 hr, at least 2000 g/m²/24 hr, or at least 400 g/m²/24 hr. In some embodiments, the breathable layer is a cloth material having a thickness of about 0.1 mm and an MVTR of about 4200 g/m²/24 hr, which provides a very high MVTR while still providing the desiccant particulate blocking required to keep the chamber 103 free of desiccant particulate. In other embodiments, the breathable layer is a paper material coated in polyurethane with acrylic adhesive having an MVTR in a range of 400-800 g/m²/24 hr.

The desiccant material 145 can be any suitable desiccant or combination of desiccants that can be molded into the desired shape and provide the required moisture absorption. Examples of suitable desiccant materials include silica gel, activated charcoal, calcium chloride, charcoal sulfate, activated alumina, Montmorillonite clay, molecular sieve, and any combination of these materials. The desiccant material can be formed into any suitable shape, including, for example, various shapes of tablets (square, circular, rectangular, etc.), annular, semi-annular, etc. In some embodiments, the desiccant material is an off-the-shelf component in a standard off-the-shelf shape, such as a tablet shape, which can be more cost effective than a custom molded component.

Figure 8:
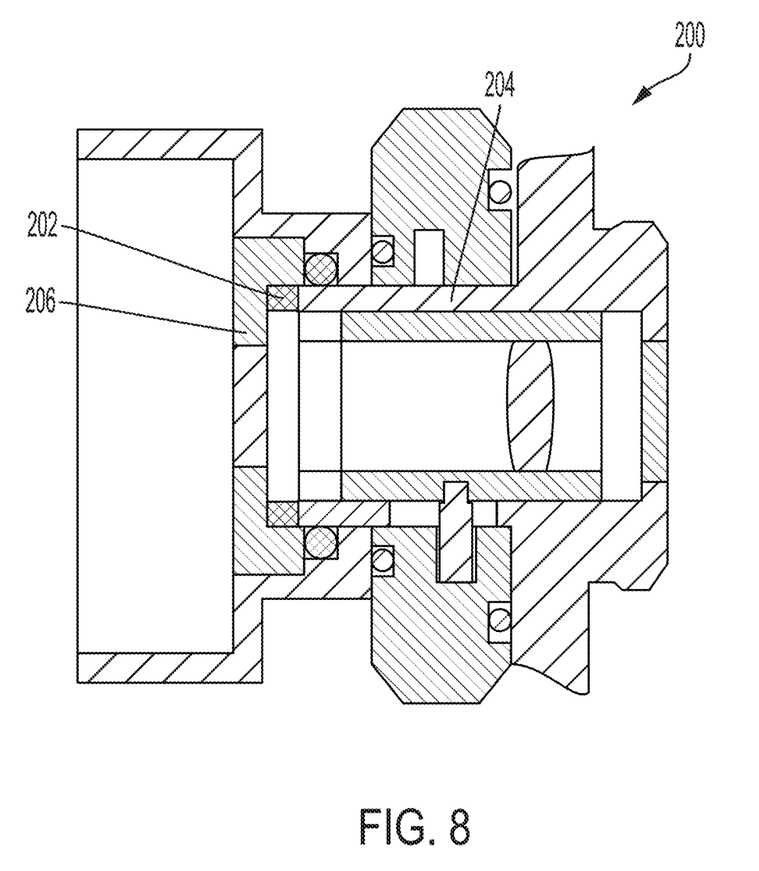
FIG. 8 illustrates a section view of an alternative placement of a desiccant component within a coupler, according to some embodiments.

FIG. 8 illustrates an alternative placement of a desiccant component 202 within a coupler 200, according to some embodiments. Coupler 200 is similar to coupler 100 and, therefore, description of similar features is not repeated for conciseness. The desiccant component 202 in coupler 200 is formed as a ring and placed in a space between the front end of the rear adapter 204 and the front end cap 206. The ring shape of the desiccant component 202 provides a greater amount of desiccant relative to the tablet shape of the desiccant components 140, which can keep the chamber 103 dryer and/or increase the lifespan of the coupler 200. The desiccant component 202 can be formed of a desiccant material molded into the ring shape and covered in a breathable material layer, as discussed above.

Desiccant components according to the principles describes above can be placed in other locations of an endoscopic camera head assembly. For example, in some embodiments, one or more desiccant components, having desiccant at least partially covered by a breathable layer, can be placed in an endoscope, such as in endoscope 12 of FIG. 1, in air communication with one or more optical components of the endoscope. The desiccant component can be positioned directly in a chamber housing the optical components, similarly to the arrangement shown in FIG. 8, or can be positioned in pockets machines in the housing of the endoscope, such as in the eyepiece portion of the endoscope, in similar fashion to the pockets of the embodiment illustrated in FIG. 4. In some embodiments, one or more desiccant components can be placed in the camera head main housing, as discussed above.

As explained above, according to various embodiments, desiccant can be positioned in a coupler of an endoscopic camera to keep the optical chamber free of moisture that may be introduced via sterilization or even during a manufacturing process. In embodiments, desiccant can additionally or alternatively be placed in one or more other components of an endoscopic camera head assembly, according to the principles described above. For example, the camera head main enclosure may include desiccant, such as described above with respect to the desiccant components 56 optionally included in the rear enclosure part 34 of camera head 13.

Figure 9:
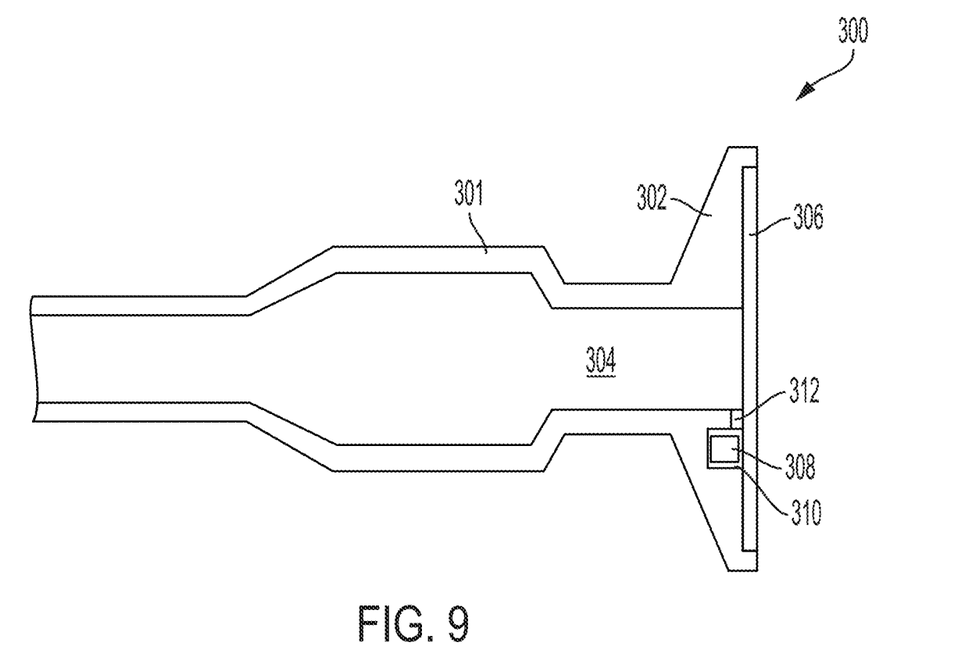
FIG. 9 is a section view of an endoscope incorporating desiccant, according to some embodiments.

According to some embodiments, desiccant can be provided in the endoscope, such as endoscope 12 of FIG. 1. An example of an endoscope with desiccant is illustrated in FIG. 9. Endoscope 300 is configured for coupling to an endoscopic camera head via a coupler, such as coupler 100 and endoscopic camera head 13. Endoscope 300 can be sterilized prior to a surgical procedure and its distal end (not shown) can be inserted into a surgical cavity for imaging the surgical cavity. Endoscope 300 may be repeatedly sterilized between surgeries, and therefore, may include desiccant, according to the principles discussed above.

Endoscope 300 includes a main body 301 that comprises an optical chamber 304 in which one or more light conveying components is positioned (such as one or more light pipes, prisms, lenses, etc.). A light transmissive component 306, such as a window or lens, may be attached to the proximal end 302, such as adhesively, to substantially seal the optical chamber 304.

To keep the optical chamber 304 dry, one or more desiccant components 308, which can be configured as described above, can be included in one or more pockets 310 formed in the main body 301. The one or more pockets 310 are in air communication with the optical chamber 304 via one or more passages 312. Thus, moisture present in the optical chamber 304 can pass via the one or more passages 312 into the one or more pockets 310 where it will be absorbed by the desiccant (e.g., by passing through the breathable cover on the desiccant).

Figure 10:
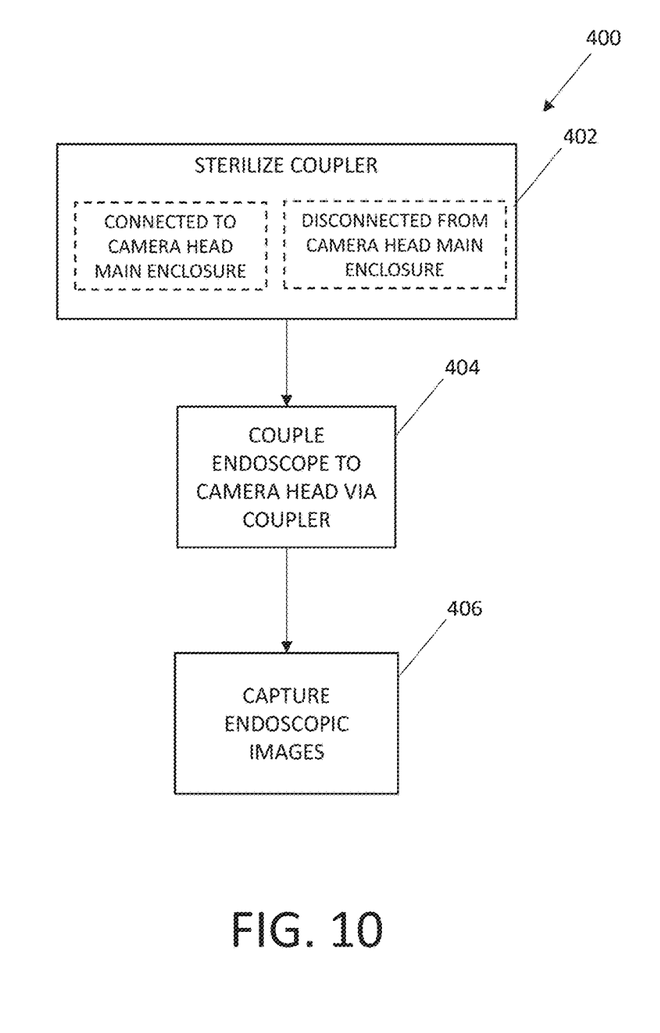
FIG. 10 is a block diagram of a method for using an endoscopic camera, according to some embodiments.

FIG. 10 is a block diagram of a method 400 for using an endoscopic camera head that includes a coupler according to the principles described herein. The endoscopic camera head can be, for example, camera head 13 of FIG. 1-3 with coupler 100 of FIG. 4 attachable thereon. The coupler can be used to couple an endoscope, such as endoscope 12 of FIG. 1, to the camera head.

At step 402, the coupler is sterilized using any suitable sterilization method. For example, in some embodiments, the coupler is sterilized using a low temperature sterilization technique. In other embodiments, the coupler may be autoclaved.

In some embodiments, the sterilization can be done with the coupler detached from the camera head main enclosure. In other embodiments, the coupler is attached to the camera head main enclosure (e.g., coupler 100 attached to main enclosure 30 of camera head 13) so that the camera head with coupler assembly is sterilized as a unit.

In various embodiments, one or more additional components may be sterilized, such as one or more endoscopes for use during a surgery.

At step 404, after the sterilization procedure, an endoscope is coupled to the sterilized camera head via the sterilized coupler. In embodiments in which the coupler was sterilized while separated from the camera head main enclosure, this step is preceded by a coupler to main enclosure assembly step.

At step 406, one or more endoscopic images is captured using the camera head (such as via system 10 of FIG. 1). The images may be capture, for example, during an endoscopic surgery or other procedure on a subject.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A coupler for coupling an endoscope to an endoscopic camera head, the coupler configured for removably mounting to a portion of the camera head that houses at least one imaging sensor, the coupler comprising:
a housing assembly comprising a clamp for releasably clamping an eyepiece of the endoscope to the coupler and an adapter configured for coupling to the portion of the camera head, the adapter comprising a cylindrical wall forming a chamber that houses at least one optical component for focusing light for the at least one imaging sensor and a flange that extends outwardly from the cylindrical wall, and
at least one desiccant component disposed within at least one pocket of the flange, the at least one desiccant component being in air communication with the chamber for absorbing moisture from the chamber, wherein the at least one desiccant component comprises a desiccant that is at least partially covered by at least one covering to prevent desiccant particulates from entering the chamber.

2. The coupler of claim 1, wherein the coupler is configured to be sterilized when dismounted from the portion of the camera head.

3. The coupler of claim 1, comprising a first light transmissive component sealing a first end of the chamber and a second light transmissive component sealing a second end of the chamber.

4. The coupler of claim 3, wherein at least one of the first and second light transmissive components is adhesively attached to the housing assembly.

5. The coupler of claim 1, wherein the at least one optical component comprises an optical assembly that comprises an optical assembly housing that houses the at least one optical component.

6. The coupler of claim 5, wherein the optical assembly comprises a plurality of optical components that are fixedly mounted to the optical assembly housing.

7. The coupler of claim 1, wherein the at least one optical component is movable within the chamber for focus adjustment.

8. The coupler of claim 1, wherein at least one air pathway leads from the at least one pocket to the chamber.

9. The coupler of claim 1, wherein the desiccant that is at least partially covered by the at least one covering is formed as a single solid.

10. The coupler of claim 1, wherein the at least one desiccant component comprises a plurality of spaced apart desiccant components.

11. The coupler of claim 1, wherein the at least one desiccant component is shaped as a tablet.

12. The coupler of claim 1, wherein the at least one desiccant component is shaped as a ring.

13. The coupler of claim 1, wherein the at least one desiccant component comprises at least one of silica gel, activated charcoal, calcium chloride, charcoal sulfate, activated alumina, Montmorillonite clay, and molecular sieve.

14. The coupler of claim 1, wherein the chamber is at least partially sealed by at least one elastomeric seal.

15. The coupler of claim 1, comprising a focusing member for engagement by a user for adjusting a location of the at least one optical component within the chamber and at least one elastomeric seal that seals between the focusing member and the housing assembly.

16. The coupler of claim 1, wherein the housing assembly comprises a plurality of components that are assembled together and at least partially sealed by one or more elastomeric seals.

17. An endoscopic camera head comprising:
a main housing that houses at least one imaging sensor; and
a coupler removably mounted to the main housing and configured for coupling an endoscope to the camera head, the coupler comprising:
a housing assembly comprising a clamp for releasably clamping an eyepiece of the endoscope to the coupler and an adapter configured for coupling to the camera head, the adapter comprising a cylindrical wall forming a chamber that houses at least one optical component for focusing light for the at least one imaging sensor and a flange that extends outwardly from the cylindrical wall, and
at least one desiccant component disposed within at least one pocket of the flange, the at least one desiccant component being in air communication with the chamber for absorbing moisture from the chamber, wherein the at least one desiccant component comprises a desiccant that is at least partially covered by at least one covering to prevent desiccant particulates from entering the chamber.

18. An endoscopic camera head comprising:
a clamp for releasably clamping an eyepiece of an endoscope to the camera head;
a cylindrical wall forming a chamber that houses at least one optical component for focusing light for at least one imaging sensor;
a flange that extends outwardly from the cylindrical wall; and
at least one desiccant component disposed within at least one pocket of the flange, the at least one desiccant component being in air communication with the chamber for absorbing moisture from the chamber, wherein the at least one desiccant component comprises a desiccant that is at least partially covered by at least one covering to prevent desiccant particulates from entering the chamber.

* * * * *